US010258734B2

(12) United States Patent
Federspiel et al.

(10) Patent No.: US 10,258,734 B2
(45) Date of Patent: Apr. 16, 2019

(54) DEVICES, SYSTEMS AND METHODS FOR CELL MODIFICATION

(71) Applicant: University of Pittsburgh—Of the Commonwealth System of Higher Education, Pittsburgh, PA (US)

(72) Inventors: William J. Federspiel, Pittsburgh, PA (US); John Alston Kellum, Pittsburgh, PA (US); Kai Singbartl, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/453,817

(22) Filed: Mar. 8, 2017

(65) Prior Publication Data

US 2017/0173254 A1    Jun. 22, 2017

Related U.S. Application Data

(63) Continuation of application No. 13/500,163, filed as application No. PCT/US2010/051772 on Oct. 7, 2010, now abandoned.
(Continued)

(51) Int. Cl.
*A61M 1/36* (2006.01)
*A61K 35/15* (2015.01)
*A61K 35/12* (2015.01)

(52) U.S. Cl.
CPC .......... *A61M 1/3689* (2014.02); *A61K 35/15* (2013.01); *A61M 1/3687* (2013.01); *A61K 2035/124* (2013.01)

(58) Field of Classification Search
None
See application file for complete search history.

(56) References Cited

U.S. PATENT DOCUMENTS 5,874,308 A * 2/1999 Kilburn ................ C07K 14/475
                                                       435/383
6,214,232 B1 * 4/2001 Baurmeister .......... B01D 61/00
                                                       210/321.75
(Continued)

FOREIGN PATENT DOCUMENTS

| WO | WO200162895 A2 | 8/2001 |
| WO | WO200224307 A2 | 3/2002 |
| WO | WO2011044329   | 4/2011 |

OTHER PUBLICATIONS

Moreno et al., J. Immunol., 177: 3218-3224 (2006).*
(Continued)

*Primary Examiner* — Thomas J. Visone
(74) *Attorney, Agent, or Firm* — Bartony & Associates, LLC (57) ABSTRACT

A method of modifying cells includes removing fluid including cells from a patient, contacting the removed fluid from the patient with at least one surface upon which at least one agent to interact at least one cell receptor is immobilized to modify cells in the fluid, and returning the fluid to the patient. The agent can, for example, be immobilized via covalent bonding or ionic bonding to the at least one surface. The fluid can, for example, be blood or a blood fraction. The agent can, for example, be an agonist, an antagonist or an inverse agonist.

13 Claims, 6 Drawing Sheets

Related U.S. Application Data (60) Provisional application No. 61/249,318, filed on Oct. 7, 2009.

(56) References Cited

U.S. PATENT DOCUMENTS

| | | |
|---|---|---|
| 7,556,768 B2 | 7/2009 | Brady |
| 2004/0185041 A1* | 9/2004 | Walker .................. A61L 2/0011 424/140.1 |
| 2007/0020142 A1 | 1/2007 | Federspiel |
| 2007/0190050 A1 | 8/2007 | Davidner |
| 2008/0175719 A1* | 7/2008 | Tracey .................. A61M 1/369 417/38 |
| 2009/0060890 A1 | 3/2009 | Humes |
| 2010/0099203 A1 | 4/2010 | Chang |

OTHER PUBLICATIONS

Videm et al., Scandinavian J. Immunol., 59:25-33 (2004).*
DiVietro, Jeffrey A., Immobilized IL-8 Triggers Progressive Activation of Neutrophils Rolling In Vitro on P-Selectin and Intercellular Adhesion Molecule-1, The journal of Immunology, 2001, 167: 4017-4025.
Extended European Search Report of counterpart European Patent Application No. 10822672.1, dated Dec. 4, 2013.
Browning, Darren D. et al.,Autocrine regulation of interleukin-8 production in human monocytes, Am J Physiol Lung Cell Mol Physiol, 279, pp. L 1129-L 1136, 2000.

* cited by examiner

DEVICES, SYSTEMS AND METHODS FOR CELL MODIFICATION

CROSS-REFERENCE TO RELATED APPLICATIONS

This application is a continuation of U.S. patent application Ser. No. 13/500,163, filed Apr. 4, 2012, which is a 35 U.S.C. 371 National Phase application of International PCT Patent Application number PCT/US2010/051772, filed Oct. 7, 2010, which claims benefit of U.S. Provisional Patent Application Ser. No. 61/249,318, filed Oct. 7, 2009, the disclosures of which are incorporated herein by reference.

GOVERNMENTAL INTEREST

This invention was made with government support under grant no. R01 HL080926 awarded by the National Institutes of Health. The government has certain rights in this invention.

BACKGROUND

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

Cell-cell interactions are central to both pathology and effective host defense to a myriad of diseases. Many cell functions are stimulated or dampened by binding of various agents, binding agents or ligands to their respective receptors on the cell surface. Ligands can, for example, include agonists, antagonists and inverse agonists. In general, agonists are able to activate a receptor. Antagonists bind to receptors but do not provoke a biological response upon binding. Binding of an antagonist disrupts interaction and inhibits function of an agonist. Inverse agonists reduce the activity of receptors by inhibiting constitutive activity of the receptor.

Modulating or modifying the surface receptor profile of cells before those cells interact with other cells inside the body has the potential to modify or program the action of those cells towards a desired response while attenuating less desired responses. Systemic drug administration can, for example, be used to modulate surface receptor profile but can also result in undesirable side effects toward other cells or tissues.

SUMMARY

In one aspect, a method of modifying cells includes removing fluid including cells from a patient, contacting the removed fluid from the patient with at least one surface upon which at least one agent to interact at least one cell receptor is immobilized to modify cells in the fluid, and returning the fluid to the patient. The agent can, for example, be immobilized via covalent bonding or ionic bonding to the at least one surface. The fluid can, for example, be blood or a blood fraction. The agent can, for example, be an agonist, an antagonist or an inverse agonist.

In a number of embodiments, the agent includes a protein or a fragment of a protein. The agent can, for example, include a cytokine. The cytokine can, for example, be a chemokine. In a number of embodiments, the agent is an interleukin. The agent can, for example, be IL-8 (interleukin 8). In a number of embodiments, the agent is a ligand selected from the group of IL-1, IL-4, IL-6, IL-8, IL-10, IL-18, IL-33, TNF, FAS, MIF, Flt3, a ligand form the Bcl-2 family of ligands, an L-selectin, a P-selectin, ICAM-1 or an antibody.

The fluid (for example, blood or a blood fraction) can, for example, be passed in a continuous loop from a blood vessel of the patient to contact the at least one surface and back to a blood vessel of the patient. The fluid can, for example, be is passed continuously for at least a period of time from a blood vessel of the patient to contact the at least one surface and back to the blood vessel or another blood vessel. The fluid can, for example, be passed discontinuously from a blood vessel of the patient to contact the at least one surface and back to the blood vessel or another blood vessel.

The fluid (for example, blood or a blood fraction) can, for example, be contacted with the at least one surface in an extracorporeal device including the at least one surface. The extracorporeal device can, for example, include a plurality of surfaces upon which at least one agent to interact with at least one cell receptor is immobilized. The plurality of surfaces can include a plurality of hollow fibers. The plurality of surfaces can include a plurality of beads.

The period of contact for cells targeted for modification can, for example, be extended. The period of contact for cells targeted for modification can, for example, be extended by the immobilization of an adhesion agent on the at least one surface, by at least one physiological characteristic of the at least one surface, or by a geometry of a volume through which the fluid containing cells flows.

Cells can, for example, be modified in treatment of sepsis, treatment of inflammatory disease, treatment of cancer, immune system regulation, or treatment of cardiovascular disease.

In another aspect, an extracorporeal device includes a vessel, an inlet adapted to pass fluid including cells removed from a patient into the vessel, at least one surface within the vessel upon which at least one agent to interact with at least one cell receptor is immobilized, and an outlet adapted to return the fluid from the vessel to the patient. The device can, for example, include a plurality of surfaces upon which at least one agent to interact with at least one cell receptor is immobilized. The plurality of surfaces can, for example, include a plurality of hollow fibers. The plurality of surfaces can, for example, include a plurality of beads. As described above, the agent can, for example, be an agonist, an antagonist or an inverse agonist. The agent can, for example, be immobilized via covalent bonding or ionic bonding to the at least one surface.

The fluid can, for example, be passed in a continuous loop from a blood vessel of the patient to contact the at least one surface and back to a blood vessel of the patient. The fluid can, for example, be passed continuously for at least a period of time from a blood vessel of the patient to contact the at least one surface and back to the blood vessel or to another blood vessel. The fluid can, for example, be passed discontinuously from a blood vessel of the patient to contact the at least one surface and back to the blood vessel or to another blood vessel.

The residence time for cells targeted for modification within the devices can, for example, be extended. The residence time for cells targeted for modification can, for example, be extended by the immobilization of an adhesion agent on the at least one surface, by at least one physiological characteristic of the at least one surface, or by a geometry of a volume through which the fluid containing cells flows.

In a further aspect, a system for modifying cells includes a first conduit adapted to be placed in fluid connection with a patient; an extracorporeal device including a vessel, an inlet in fluid connection with the first conduit, at least one surface within the vessel upon which at least one agent to interact at least one cell receptor is immobilized, and an outlet; a second conduit in fluid connection with the outlet and adapted to be placed in fluid connection with the patient; and at least one pump system to circulate fluid from the patient through the system.

The technology described herein, along with the attributes and attendant advantages thereof, will best be appreciated and understood in view of the following detailed description taken in conjunction with the accompanying drawings.

DETAILED DESCRIPTION

As used herein and in the appended claims, the singular forms "a," "an", and "the" include plural references unless the content clearly dictates otherwise. Thus, for example, reference to "an agent" includes a plurality of such agents and equivalents thereof known to those skilled in the art, and so forth, and reference to "the agent" is a reference to one or more such agents and equivalents thereof known to those skilled in the art, and so forth.

As opposed to systemic drug administration, devices, systems and/or methods in which blood is perfused through a system external to the body (for example, an extracorporeal hemoperfusion system), wherein one or more internal surfaces of the external or extracorporeal system include immobilized agents to interact with one or more cell receptors, offers the opportunity to manipulate, modulate, modify or program circulating cells outside the human body in a well-defined environment. In this manner, circulating cells can be directly targeted while undesirable side-effects towards other cells or tissues are limited.

The extracorporeal devices, systems and methods hereof provide a platform that can be applied to numerous conditions and diseases involving circulating cells, such as atherosclerosis, cancer, HIV, sepsis and many others. By altering the behavior of circulating cells in a defined manner, it is possible to treat disease in a fundamentally different manner than previously.

In a number of representative studies, the modification or reprogramming of white blood cells (neutrophils) was demonstrated. The incubation of isolated white blood cells (neutrophils) with immobilized cell activators (chemokine CXCL1) leads to selective downregulation of the respective receptor on neutrophils over time. That process effectively renders the cells unresponsive to activation and thus fundamentally changes their biology.

This devices, systems and/or methods hereof can readily be adapted or extended to alter the responses of various cells and in a variety of different ways (for example, increasing or decreasing their responses to a variety of stimuli). Interaction of agents, binding agents or ligands with cell receptors or binding partners on a cell can, for example, modify surface receptor, modify cellular function, modify cellular activity, modify cellular phenotype, etc., thereby modifying (modulating, increasing, decreasing, or otherwise changing) an activity or specificity of the cell. The devices, systems and/or methods hereof can be applied to virtually any condition in which circulating cells are involved in pathology or mitigation of disease. Although white blood cells such a neutrophils are modified in several representative studies hereof, many types of cells can be modified via the interaction with immobilized agent with cell receptors.

Modulating or modifying cells via, for example, modulating or modifying surface receptor profile of cells before the cells interact with other cells inside the body provide a platform to program the action of these cells towards a desired response while attenuating less desired responses.

In a number of representative studies, they chemokine interleukin-8 or IL-8 was immobilized on a surface to interact with its neutrophil surface receptors. Cytokines are cell-signaling molecules secreted by a number of cells and used extensively in intercellular communication. Chemokines are a type of cytokine which are named for their ability to not only perform the immunoregulatory functions characteristic of many cytokines but also for their ability to induce chemotaxis (that is, cellular movement or migration) of leukocytes by binding to specific receptors on their surface. Chemokines bind to G-protein-coupled receptors (GPCRs) on the leukocyte surface, causing internalization and consequently degradation or recycling of the receptor to occur. The activation of leukocytes via chemokine binding leads to cellular migration during times of both routine immunomodulation and inflammation. Often, surface GPCRs bind several different chemokines, such as IL-8 binding to the chemokine receptors CXCR1 and CXCR2. Using chemokine naming conventions, IL-8 is also known as CXCL8, representing the ligand of a CXC chemokine which by definition has two amine-terminated cysteine residues separated by a single amino acid residue. Of all 15 identified CXC chemokines, IL-8 displays the greatest ability to induce migration of neutrophils to sites of inflammation.

Although small amounts have been identified on other cell types, both CXCR1 and CXCR2 are expressed almost exclusively on monocytes and neutrophils. It has been showed that IL-8 downregulated over 90% of its neutrophil surface receptor within 10 min at 37° C. That data suggests that IL-8 is a good candidate for GPCR antagonism. Downregulation of receptors after binding with chemokines is achieved through internalization, which occurs by a number of different mechanisms. For the case of IL-8 binding to CXCR1 and CXCR2, the receptors undergo phosphorylation in their carboxyl-terminus and intracellular loops by G protein-coupled receptor kinases (GRKs). The G protein subunits then uncouple from the subunits and the phosphorlyated areas become associated with adaptor molecules β-arrestin and adaptin 2 (AP-2). Clathrin is then recruited by the adapter molecules and clathrin-coated pits are formed. These pits become clathrin-coated vesicles through the localization of dynamin and its ability to cause the pits to encapsulate themselves and pinch off from the membrane. Internalization occurs when the vesicle becomes uncoated and is taken up into the early endosomal compartment. From here, the chemokine receptor can take one of two actions: it can enter the perinuclear compartment and be recycled to the plasma membrane where it will be reexposed to ligand, or it can move on to the late endosomal compartment where it will eventually be sorted and degraded. Most of the chemokine receptor is recycled to the plasma membrane.

Figure 1:
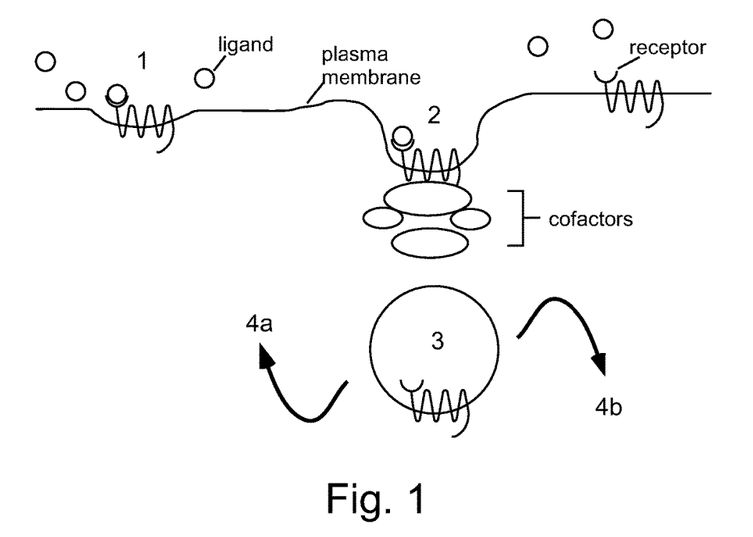
FIG. 1 illustrates a mechanism for G-protein-coupled receptor ligand internalization.

FIG. 1 shows a diagram of proposed steps associated with GPCR internalization after chemokine binding. In the illustrated mechanism for GPCR internalization, chemokine binds to a cell receptor (1). A clathrin-coated pit is then formed and association with various cofactors occurs (2). A clathrin-coated vesicle is then formed (4). Subsequently, either recycling (4a) or degradation (4b) occurs.

IL-8 receptor downregulation has been well-characterized but very little is known about the requirements for binding. Although both free and bound IL-8 are found in vivo, one study suggested that tethering to glycoasaminoglycans (GAGs) on the extracellular matrix and endothelial cell wall is necessary to maintain the in vivo activity of chemokines. Prior to the present studies, little was known about whether or not ex vivo binding of IL-8 to its receptors could be accomplished without GAG anchoring or presence in free solution.

Additionally, the question remained as to whether or not IL-8 or other agents or ligand are internalized with its cell-surface receptors after binding. Until the present studies, it had not been demonstrated that cell receptor interactive agents immobilized upon a surface via, for example, atomic bonds (covalent or ionic bonds) could interact with cell receptors to modify cells in the manner that free cell receptor interactive agents have been shown to do.

Figure 2A:
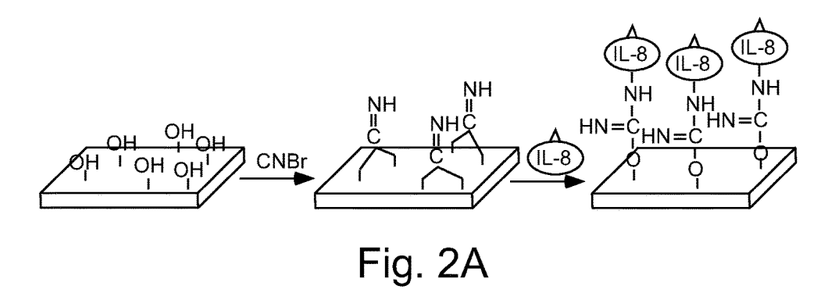
FIG. 2A illustrates an embodiment of method to covalently immobilize interleukin 8 or IL-8 upon a surface including hydroxyl groups.
Figure 2B:
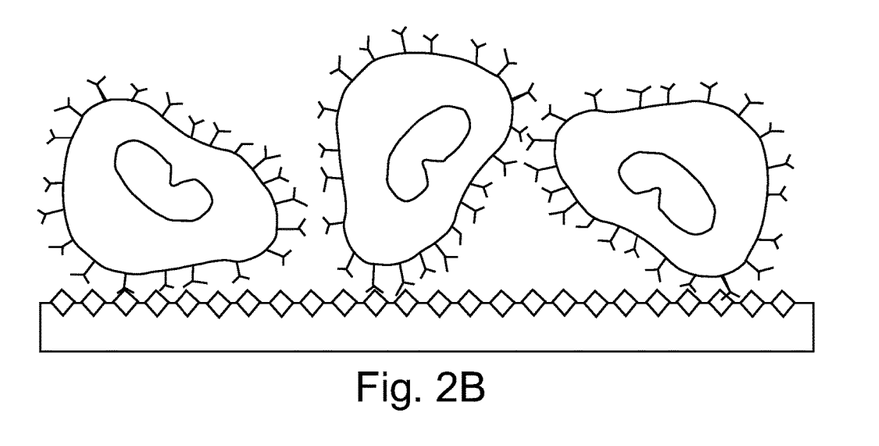
FIG. 2B illustrates an idealized schematic representation of the interaction of neutrophils with immobilized IL-8 and/or other agents.

Representative studies hereof indicate that covalently immobilized IL-8 can modify neutrophils in a manner to disable migratory action of the neutrophils in response to a chemotactic gradient as free IL-8 is known to do. The migratory action of polymorphonuclear neutrophils (PMNs) is mediated by CXCR1 and CXCR2, both of which bind to IL-8. While low concentrations of IL-8 (10-50 ng/ml) trigger activation and migration of white blood cells, while high concentrations (~1000 ng/ml) cause migratory activity to shut off. Downregulation of chemotaxis and subsequent expression of more inflammatory mediators may be a potential new treatment for sepsis.

Activation of PMNs in response to inflammation causes the release of cytokines such as TNF and interleukin-12, and of chemokines such as macrophage inflammatory protein (MIP)-1α, MIP-3α, and MIP-1β. The increased expression of these inflammatory mediators contributes to the worsening immune response seen in septic patients. Experiments in which the gene encoding for CXCR2 (the only murine IL-8 receptor) in mice was deleted showed that the mutant mice did not develop sepsis in a peritonitis model, whereas control animals did. In has been shown that the receptors to IL-8 are globally inactivated by agonist concentrations above a certain threshold, which has been hypothesize to correspond to neutrophils reaching the site of inflammation in vivo. It has also been shown that the CXCR1 and CXCR2-targeted chemokine receptor pepducins (lipid-conjugated peptides which selectively inhibit GPCR signaling) prevent IL-8 from binding and significantly reduce mortality in mice undergoing cecal ligation and puncture (CLP) as a model for sepsis. It was further shown a pepducin for CXCR4, a neutrophil surface receptor which has an effect on migration but does not bind IL-8, had no effect on survival up to 9 days after CLP despite showing a similar decrease in migratory activity.

The effect of immobilized IL-8 on its neutrophil receptors was investigated using cellulose fibers as a substrate for immobilization. Cellulose contains exposed hydroxyl groups which can readily be modified for protein immobilization. Well-characterized cyanogen bromide (CNBr) activation chemistry was used. That procedure created extremely reactive cyanate ester groups on the fiber surface which could become inert carbamate groups or cyclic imidocarbamates which react with exposed amine groups on the ligand IL-8. Fifty cellulose triacetate fibers were removed from a hollow fiber dialyzer (Baxter CT110G) and cut to 4.5 cm each, giving a total surface area of 14.3 $cm^2$. The fibers were rinsed with deionized for 30 min and swollen in 0.2N NaOH for 1 h on ice. The fibers were next rinsed with a 1:1 ratio of 0.1M ice cold sodium bicarbonate buffer (0.1M $NaHCO_3$, pH 8.5) and 0.5M ice cold NaCl at pH 8.3 for 15 min. CNBr was dissolved in 0.2 N NaOH (0.5 g in 5 ml) and incubated with the fibers for 1 h, using 10N NaOH to maintain the pH above 11.0 and ice to keep the temperature at 25° C. The fibers were then rinsed two times each with deionized water and sodium bicarbonate buffer. IL-8 was immobilized by incubating the fibers with 25 μg of recombinant human IL-8 (Invitrogen) in 0.1M sodium carbonate buffer at pH 8.5 on a shaker at 4° C. overnight. The fibers were then washed with 200 ml each of 1.0M NaCl and DI water. To block any remaining active groups, the fibers were incubated with 100 ml of 1.0M ethanolamine for one hour. Fibers were then washed once again with 200 ml each of 1.0M NaCl and DI water. FIG. 2A illustrates the process of CNBr activation of cellulose wherein an intermediate imine is formed which reacts with secondary amine groups on IL-8, forming a covalent bond. FIG. 2B illustrates an idealized schematic representation of the interaction of neutrophil receptors with immobilized IL-8 and/or other immobilized ligands.

Figure 3:
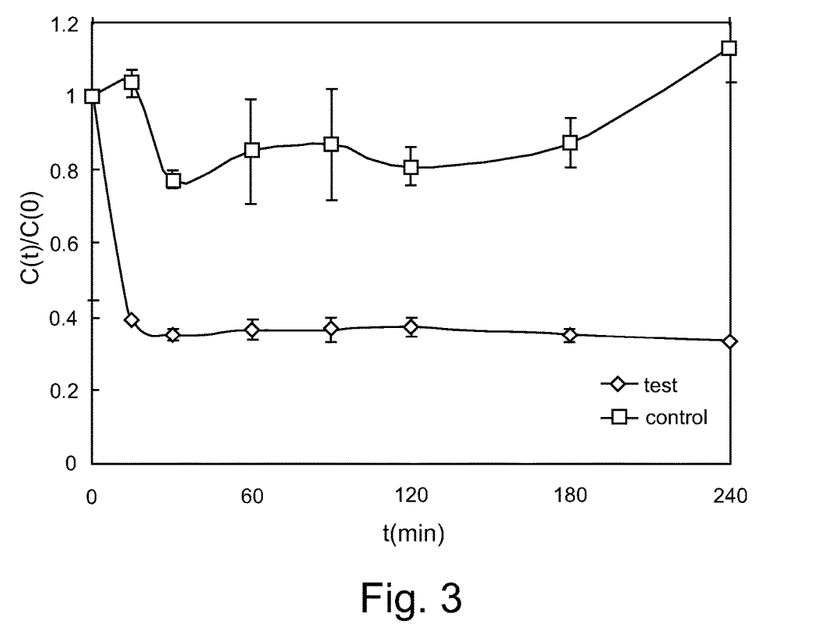
FIG. 3 illustrates a study of anti-IL-8 capture using cellulose fibers modified with immobilized IL-8 and unmodified cellulose fibers.

To confirm the presence of IL-8 on the cellulose fiber pieces, biotinylated anti-IL-8 (available from Invitrogen Corporation of Carlsbad, Calif.) capture was performed in a batch experiment. These results were compared to results from batch capture of biotinylated anti-IL-8 antibodies using unmodified fibers. Fibers were mixed continuously with a solution of 20 µg anti-IL-8 in 15 ml of PBS with 0.05% Tween 20 added to prevent protein aggregation. 100 µl samples were taken before starting the experiment and again at 15, 30, 60, 90, 120, 180, and 240 min. Anti-IL-8 concentration was determined using a modified ELISA technique. A 96-well polystyrene microwell plate was incubated overnight at 4° C. with 25 µg of IL-8 in 5 ml of sodium carbonate coating buffer (100 µl per well). Wells were washed and then blocked with 1% BSA in PBS for 2 h at 37° C. Wells were washed again and then incubated with 100 µl of biotinylated anti-IL-8 standards or samples. Streptavidin-linked horseradish peroxidase was conjugated to the biotinylated antibodies and the optical density associated with the color change that takes place when chromagen was added was read at 450 nm. ELISA data for anti-IL-8 capture as set forth in FIG. 3. The results show that the test fibers contained IL-8 and the control fibers did not. Thus, the immobilized IL-8 retained its ability to bind anti-IL-8 with high affinity following immobilization while the control fibers (containing no IL-8) showed no affinity for IL-8.

Figure 4:
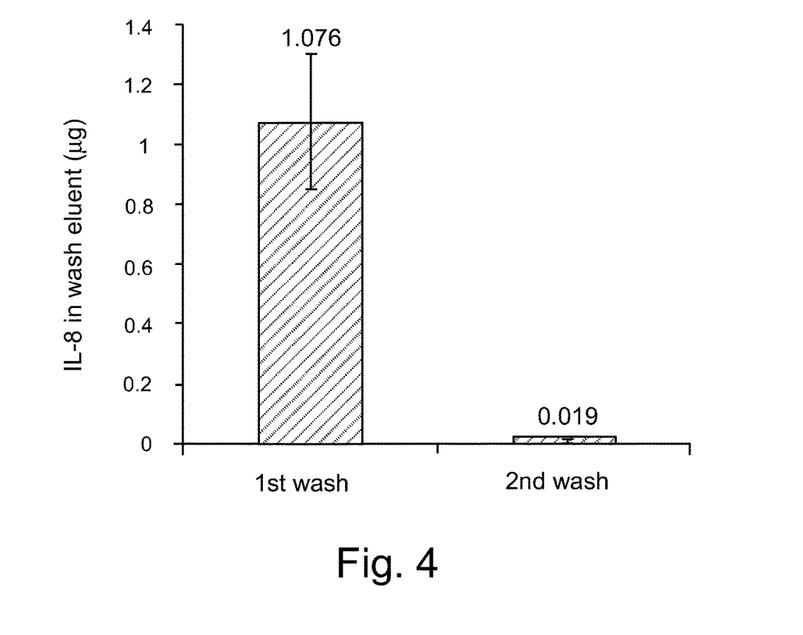
FIG. 4 illustrates IL-8 loss during immobilization (in μg) as measured using enzyme-linked immunosorbent assay (ELISA) on wash eluent samples following the immobilization procedure.

FIG. 4 illustrates IL-8 loss during immobilization (in µg) as measured using ELISA on wash eluent samples following the immobilization procedure. A degree of immobilization as defined below was determined to be 96%.

$$\text{Degree of immobilization} = 100\% - \frac{\text{Mass of } IL\text{-}8 \text{ in wash eluent}}{\text{Starting mass of } IL\text{-}8} = 96\%$$

Figure 5:
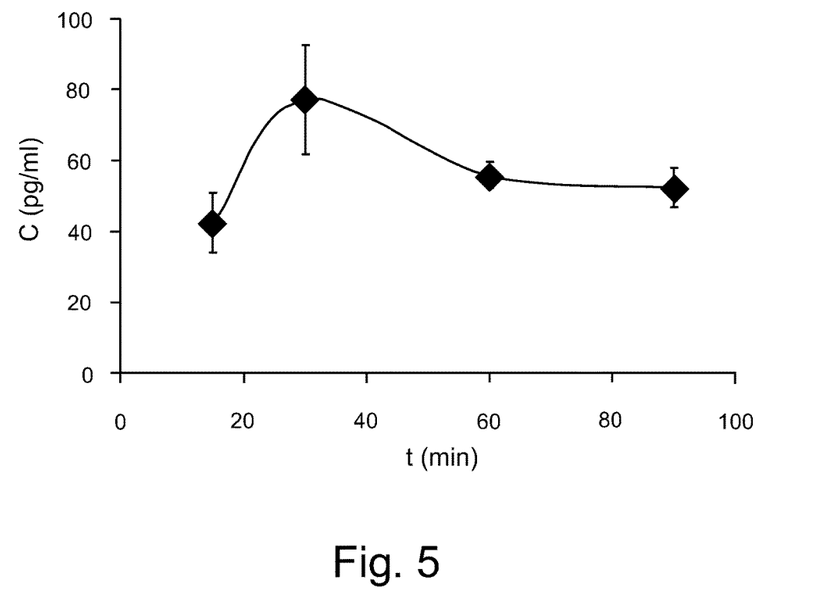
FIG. 5 illustrates a study of IL-8 leaching into buffer (in pg IL-8/ml buffer) during a 90 minute incubation in the buffer wherein less than 0.01% of immobilized IL-8 was lost during the incubation.

After immobilization, the IL-8-immobilized fibers were incubated with a buffer solution for 90 min to determine if any significant amount of IL-8 would leach off into blood. No significant loss (that is, <0.01%) of IL-8 observed over the time course of the experiment. Data from that study are illustrated in FIG. 5. It is desirable to minimize leaching of immobilized agent into the fluid (for example, blood). Therefore, relatively high affinity immobilizing techniques can be used including, for example, covalent bonding, ionic bonding, and adsorption. In many cases, covalent bonding and/or ionic bonding can be used to reduce or minimize leaching of immobilized agent.

Figure 6A:
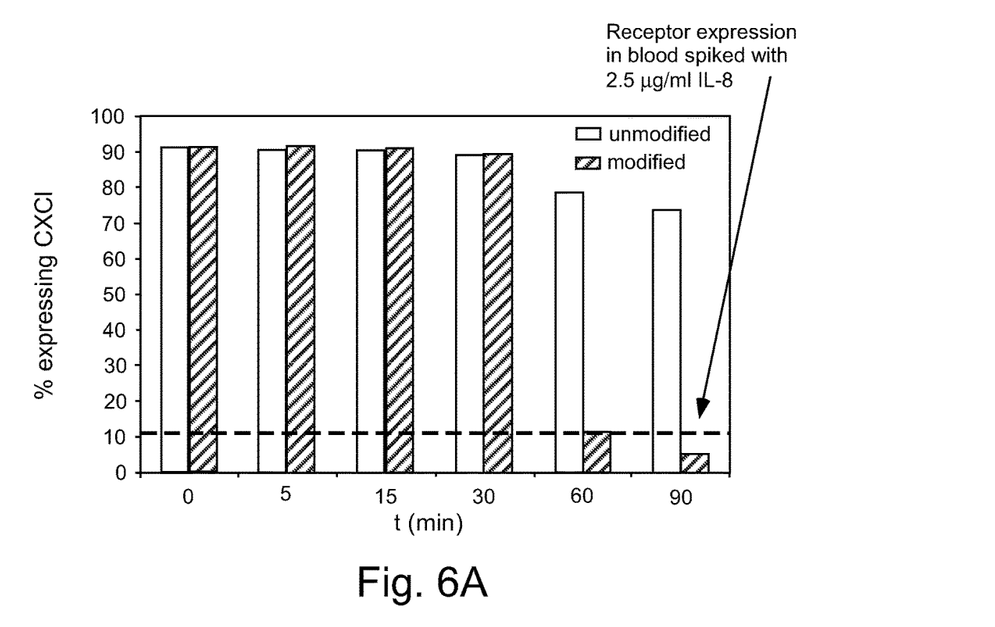
FIG. 6A illustrates CXCR1 expression over time during incubation with IL-8-modified/immobilized fibers and unmodified fibers wherein the dashed line represents CXCR1 expression in a sample of blood spiked with free IL-8.
Figure 6B:
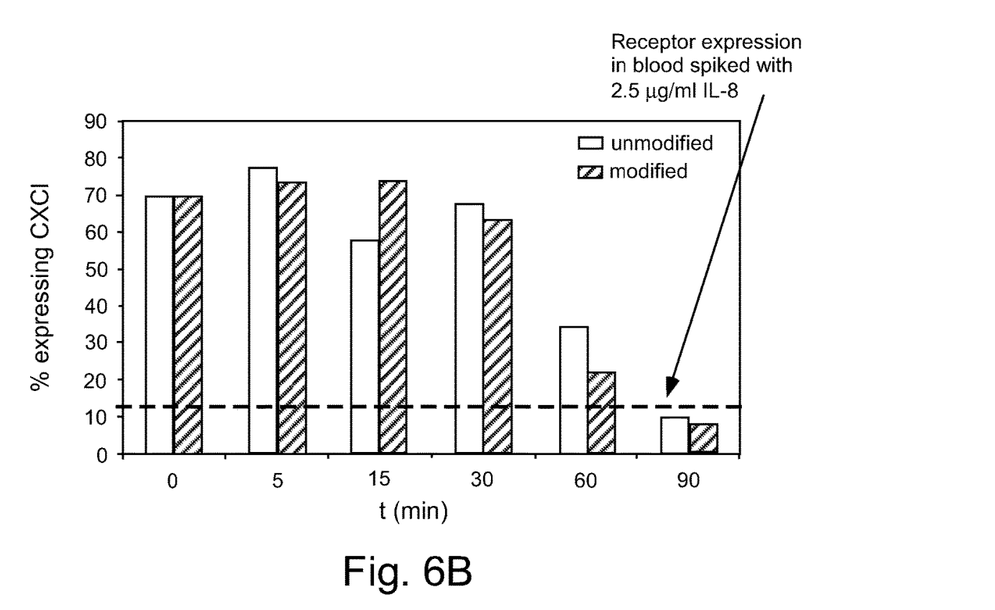
FIG. 6B illustrates CXCR2 expression over time during incubation with IL-8-modified/immobilized fibers and unmodified fibers wherein the dashed line represents CXCR2 expression in a sample of blood spiked with free IL-8.

After the presence of IL-8 was confirmed on the cellulose fibers, a new batch of modified fibers was prepared and incubated with 15 ml of healthy human blood with sodium heparin added as an anticoagulant. The blood was gently mixed throughout the experiment and 500 µl samples were taken at 5, 15, 30, 60, and 90 min and stored on ice until assay with flow cytometry. Blood incubated with unmodified cellulose fibers was used as the negative control, and the positive control was obtained by incubating blood with 5 µg/ml free IL-8. Neutrophil expression of the receptors CXCR1 and CXCR2 was quantified using a Beckman Coulter Epics XL-MCL flow cytometer. Anti-CXCR1 PE-Cy5 conjugated antibodies (available from BD Biosciences of San Jose, Calif. under BD catalog number 551081) and anti-CXCR2 FITC conjugated antibodies (BD catalog number 551126) were used to label the receptors. Cells were sorted into monocyte and then PMN fractions and analyzed. The results of this experiments are set forth in in FIGS. 6A and 6B. As illustrated in FIG. 4A, expression of CXCR1 significantly decreased over time compared to the control. As illustrated in FIG. 4B, both the test and control fibers resulted in a decrease in CXCR2 expression. The reason for the decrease in CXCR2 expression using control fibers is unclear, but may be the result of external factors causing activation of neutrophils.

As set forth above, GAG binding can be of importance for in vivo chemokine activity. A hypothesis is that in some chemokines, including IL-8, the active site for endothelial GAG linkers such as protamine sulfate or heparin sulfate is spatially separated from the active site for its cell surface GPCRs. The interaction of immobilized IL-8 with CXCR1 and CXCR2 may, for example, be enhanced by first immobilizing (with, for example, 10 mg/ml) the GAG heparin on the cellulose fibers, followed by IL-8 immobilization on heparin. GAG immobilization on cellulose membranes can be effected using the same CNBr chemistry as set forth above for IL-8 immobilization.

It has been observed that IL-8 interactions with neutrophils in a flowing environment can be enhanced by slowing of the neutrophils using adhesion molecules. In a number of embodiments, adhesion molecules such as p-selectin and intracellular adhesion molecule-1 (ICAM-1) can be immobilized at physiologically relevant concentrations (for example, concentrations of 0.3 and 0.1 µg/ml, respectively) onto, for example, cellulose membranes.

Receptor expression may, for example, be diminished both initially and for a finite time after contacting IL-8 while recycling takes place. Based on previous studies, the time required to achieve maximum internalization may, for example, be 30-60 min after contacting IL-8 and the time for recycling may, for example, be approximately 90-180 min after contacting IL-8. Sufficient or optimal contact or residence time for a cell/immobilized agent system is readily via routine evaluation. As described above, the inclusion of adhesion molecules can slow down neutrophil rolling. Moreover, receptor expression can be further diminished if oriented binding can be achieved using GAG linkers. If, for example, adhesion molecules are not sufficient to slow down neutrophils enough for sustained interaction with immobilized IL-8, slower flow rates or a system where flow can be stopped and restarted periodically can be utilized in an extracorporeal device or system.

Furthermore, slowing or sequestering of cells targeted for modification via immobilized agents or ligands (such a white blood cells or specifics white blood cells) can also or alternatively be accomplished using, for example, a packed bead device with relatively small interstitial spaces. In a number of studies, blood was withdrawn from either septic patients or healthy volunteers. Blood was circulated through miniaturized extracorporeal ex vivo circuits with either standard beads or small beads. Blood samples were obtained and white blood cell (WBC) counts (with differential measurements) were obtained. After 4 hours of circulation in these closed loop circuits, another blood sample from each circuit was obtained and WBC counts determined.

Figure 7A:
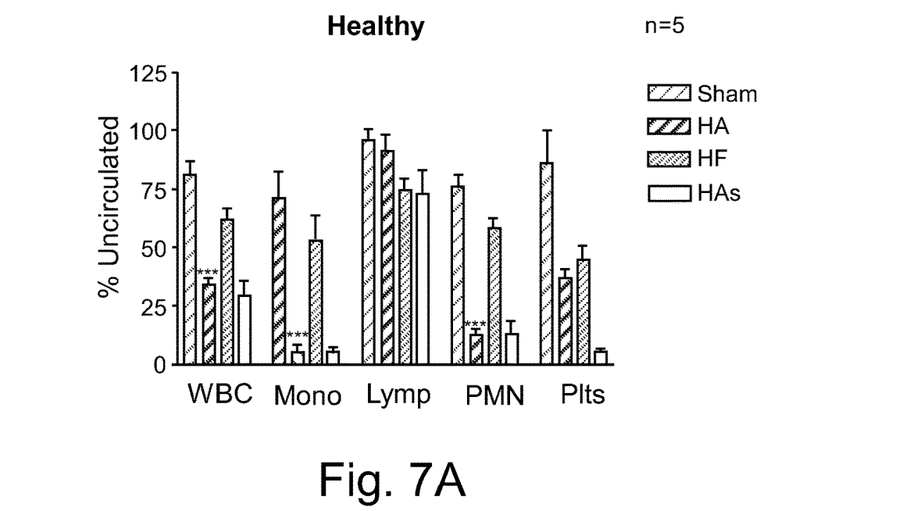
FIG. 7A illustrates the results of white blood cell counts for heparinized blood from healthy volunteers (n=5) recirculated at a flow rate of 0.5 ml/min for 4 hours (using a 20 ml reservoir) through an empty device including no sorbent (Sham), through a hemofiltration circuit (HF), through a device including standard size beads (HA) and a through a device including smaller sized beads (HAs).
Figure 7B:
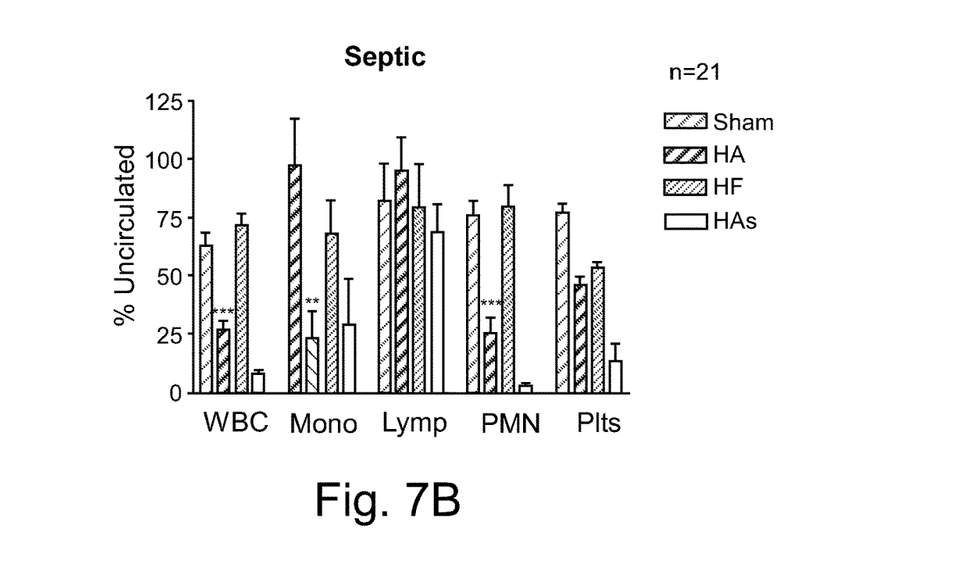
FIG. 7B illustrates the results of white blood cell counts for heparinized blood from patients with sepsis (n=21) recirculated at a flow rate of 0.5 ml/min for 4 hours (using a 20 ml reservoir) through an empty device including no sorbent (Sham), through a hemofiltration circuit (HF), through a device including standard size beads (HA) and a through a device including smaller sized beads (HAs).

FIGS. 7A and 7B the results of experiments conducted using a closed loop with miniature devices containing 1 gram of sorbent beads for blood from health patients and blood from septic patients, respectively. Heparinized blood from healthy volunteers (n=5) or patients with sepsis (n=21) was recirculated at a flow rate of 0.5 ml/min for 4 hours using a 20 ml reservoir. As controls, a sham circuit was used with an empty device (no sorbent) as well as a hemofiltration circuit (HF). FIGS. 7A and 7B illustrate results from the standard size bead device (HA) and a smaller bead device (HAs). White blood cells were removed (70-90%) by these devices compared to much smaller changes for the sham device and HF device. Furthermore, lymphocytes were not substantially effected by the devices while the target cells, neutrophils (PMN) and monocytes (Mono) were captured. Electronic microscopy photographs for both the smaller beads and the standard beads confirmed the presence of neutrophils and monocytes thereon.

The above studies confirm that a device using a geometry of, for example, spherical elements or beads (narrow channels between beads) can be used to selectively sequester neutrophils and monocytes (while excluding lymphocytes and red blood cells). Platelets are also removed. Without limitation to any mechanism, neutrophils and monocytes may tend to settle onto the surfaces of the beads because of the adhesion molecules of these cells whereas other cells tend to glide past. In nature, neutrophils and monocytes tend to enter tissue more than, for example, lymphocytes. Neutrophils and monocytes are more "programmed" to latch onto the surfaces. The sorbent beads used for these experiments were obtained from CytoSorbents, Inc. of Monmouth Junction, N.J. and are constructed of a polystyrene divinyl benzene copolymer.

Figure 8:
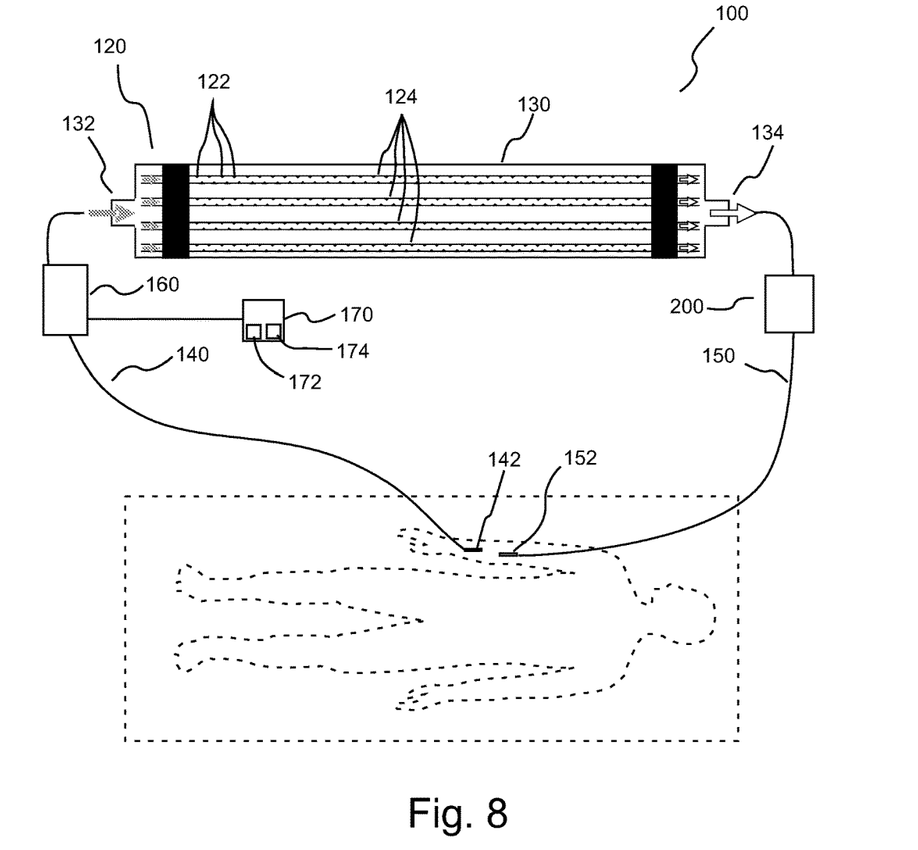
FIG. 8 illustrates an embodiment of a system including an extracorporeal device including a plurality of hollow fibers having a cell receptor ligand such as IL-8 immobilized thereon.

FIG. 8 illustrates an embodiment of an extracorporeal system 100 including an extracorporeal device 120 in which a receptor interactive agent or ligand 122 (for example, a cytokine such as IL-8) is immobilized onto the inner lumen of hollow fibers 124 within a housing 130. Housing 130 includes an inlet 132 via which cell-containing fluid (for example, blood of a blood fraction) from a patient enters housing 130 and an outlet 134 via which fluid is returned to the patient. Inlet 132 can, for example, be placed in fluid connection with a blood vessel of a patient via a conduit 140 (which can, for example, include a catheter 142) to deliver blood from the patient to extracorporeal device 120. Outlet 134 can, for example, be placed in fluid connection with a blood vessel of the patient via a conduit 150 (which can, for example, include a catheter 152) to deliver blood including modified or programmed cells to the patient from extracorporeal device 120. One or more pump systems 160 such as a peristaltic pump can, for example, be placed in fluid connection with conduit 140. A control system 170 (for example, comprising at least one processor 172 and at least one memory system 174 in communication therewith) can, for example, be in operative communication with pump system 160 and/or other flow control systems (for example, valves (not shown); air detection systems, temperature control systems etc. to control flow through and operation of system 100.

Fibers 124 can, for example, be potted in a manifold manner at each end of housing 120 so that the inlets thereof are in fluid connection with inlet 132 and the outlets thereof are in fluid connection with outlet 134. Fibers such a cellulose fibers can, for example, be potted into polymeric/plastic modules (for example, polycarbonate modules) using, for example, UV curing glue (available, for example, from Dymax Corporation, USA of Torington, Conn.). The elements of housing 130 can, for example, be formed from a polymeric material such as polycarbonate. Immobilization can be achieved as described above by circulating the solutions through used in the immobilization device 120 using pump system 160 (for example, a peristaltic pump).

IL-8 and/or other agents can, for example, be immobilized within device 120 a part of a therapy for sepsis. System 100 can, for example, be operated in the manner of a hemofiltration device in a relatively slow continuous, partially continuous and/or batch process.

System 100 or device 120 can, for example, be used in connection with other devices and/or systems. In the treatment of, for example, sepsis, other inflammation and immune system responses and/or other conditions, system 100 can, for example, be used in connection with one or more hemoadsorption systems (represented schematically as system 200 in FIG. 7) for removal of, for example, cytokines (for example, using CytoSorb™ beads available from MedaSorb Technologies Corporation of Monmouth Junction, N.J.). See, for example, U.S. Pat. No. 7,556,768.

In the embodiment of device 120 described above, binding agents 122 are immobilized on the interior wall of the lumens of fibers 124. The cell-containing fluid flows through the lumens so that cells can interact with the immobilized agents. Alternatively, interactive agents can be immobilized on the exterior of fibers 124 and the cell-containing fluid can flow through the volume surrounding fibers 124. In the case of agents adapted to interact with white blood cell, it can be advantageous to immobilize such agents on the interior wall of a lumen or other flow channel or conduit as white blood cells tend to flow along the walls of blood vessels.

The immobilized agents hereof can be immobilized on many types of surface conformations including hollow fibers as described above, membranes or sheets, beads etc. Moreover, many types of surface compositions can be used (for example, polymeric surfaces, glass surfaces, etc.) In a number of surface immobilizations techniques, actions taken to effect immobilization onto the surface can include one or more of the following: 1) chemical modification of the surface, 2) activation of the functional groups that have been exposed on the surface, and 3) covalent or ionic coupling of the agent or ligand to the surface via interaction/reaction of one or more functional groups on the surface with one or more functional groups of the agent or ligand. Many different surface immobilization chemistries have been developed for various applications which can readily be used herein. In addition to the cyanogen bromide activation chemistry discussed above, which can be used in connection with a wide variety of surfaces and agents, many agents include reactive hydrogen groups (for example, hydroxyl groups, amine groups and/or thiol groups) which can for example, be reacted with isocyanate functionality to immobilize an agent upon a surface. For example, agents can be immobilized within a polyurethane composition via reaction with isocyanate groups during polymerization.

Figure 9:
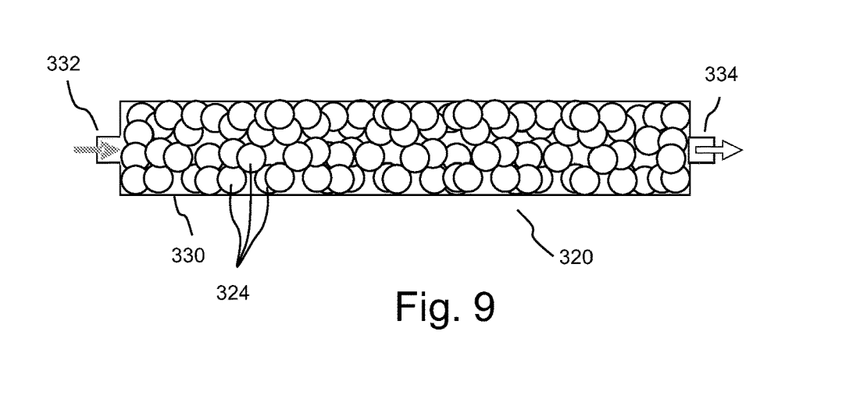
FIG. 9 illustrates an embodiment of an extracorporeal device including a plurality of beads having a cell receptor ligand immobilized on the surfaces thereof.

FIG. 9, for example, illustrates an embodiment of an extracorporeal device 320 including a plurality of beads 324 upon which one or more binding agents are immobilized (for example, via covalent bonding). As described in connection with device 120, device 320 includes a housing 330 which includes an inlet 332 via which cell-containing fluid from a patient enters housing 330 (wherein the fluid flows through the interstitial volume between beads 324) and an outlet 334 via which fluid is returned to the patient.

As described above, many types of agents can be immobilized in the extracorporeal devices hereof for use in a variety of clinical applications. For example, in the treatment of sepsis and/or system inflammation, down regulating the response to various ligands decreases cell activation and chemotaxis with the result of decreased organ injury. Up regulation of the response to various molecules results in increased bacterial killing and change in leukocyte trafficking.

With respect to cytokines, in addition to interleukins such as IL-8, a variety of cytokines/chemokines, including CXRC1-8 ligands can be immobilized for interaction with corresponding receptors. Interleukins such as IL-1, IL-4, IL-6, IL-8, IL-10, IL-18, and IL-33 can, for example, be immobilized in connection with treatment of, for example, sepsis and/or inflammatory diseases.

Further, ligands for interaction with the tumor necrosis factor receptor families can be immobilized (for example, TNF for TNFr1/r2 receptors, FAS ligand for FAS receptors (which also directly affect PMN apoptosis) in connection with treatment of, for example, sepsis and/or inflammatory diseases.

Cytokine macrophage migration inhibitory factor (MIF) can also be immobilized in connection with treatment of, for example, sepsis and/or inflammatory diseases.

Various binding agents or ligands for toll-like receptors can be immobilized. Toll-like receptors are a class of proteins that play a role in the innate immune system. These receptors on the surface of various cells recognize molecules or agents from bacterial cell walls, viral DNA and other pathogen-associated molecular patterns as well as damage-associated molecular patterns. By signaling through these receptors via immobilized binding agents, cells can be made to be more activated or down regulated to a given response.

Immobilized binding agent in an extracorporeal device can also be used in connection with clinical applications for cancer and transplantation. The interaction between the immune system and "foreign" tissues involves a series of events that begin with recognition of foreign antigens. When the tissues in question are from a tumor, the goal is to increase recognition by the immune system. In the case of transplantation, the goal is to have the immune system ignore these tissues. Immobilized binding agents can, for example, be used in activation of natural killer cells and in cell differentiation into natural killer cells. Examples of ligands include, but are not limited to, Flt3 ligand (which may also be used in connection with anti-viral therapy), IL-2 and ligands for CD4/CD25 positive T-cells (regulatory T-cells). In the case of modulation of auto-immunity, the Bcl2 family of ligands (including, for example, Bim) can be immobilized.

Binding agents can also be immobilized for use in connection with clinical applications for cardiovascular disease. For example, myocardial infraction and stroke involve a complex interplay between circulating cells (leukocytes and platelets) and endothelial cells. Modulation of the interactions between these cells can be important for the prevention and treatment of many forms of cardiovascular disease. For example, in the case of atherosclerotic plaque formation/rupture, binding agents or ligands for selectins such as L-selectins and/or P-selectins can be immobilized (for example, P-selectin glycoprotein ligand or PSGL). Intercellular adhesion molecule 1 or ICAM-1, which is a ligand for integrins, can also be immobilized. For inhibition of post-ischemic inflammation, binding agents for selectins, FAS/FAS Ligand, and/or Bcl-2 ligand can be immobilized.

With respect to vaccination and immune stimulation, the process of making an effective vaccine can be complex and can represent some risk since live attenuated viruses can sometimes cause disease particularly in immuno-compromised patients. Antigen-cell interactions involve antigen processing and complex cell-cell interactions. In several embodiments, antigen reactions can be produced by presenting immobilized antigen to cells in ways that resemble what macrophages and similar cells do in the normal host response. This methodology would improve the number of vaccines one could develop, extending application of the devices, systems and methods hereof to treatments of retroviruses (for example, HIV) and other difficult to manage diseases.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of modifying cells comprising:
   placing an inlet of an extracorporeal device in fluid connection with a circulatory system of a patient,
   placing an outlet of the extracorporeal device in fluid connection with the circulatory system of the patient,
   removing blood from the circulatory system of a patient via the inlet to pass the blood, which includes target neutrophil cells, into the extracorporeal device,
   inducing flow of the blood through the extracorporeal device at a flow rate resulting in a cell residence time suitable for recirculation of the blood to the patient, at least one surface within the extracorporeal device comprising IL-8 (interleukin 8) immobilized thereon via covalent or ionic bonding,
   releasably interacting the IL-8 with the at least one cell surface receptor of the target neutrophil cells as the target neutrophil cells flow within the blood thereover to modify surface receptor expression of the target neutrophil cells and release target neutrophil cells with modified surface receptor expression back into the flow of the blood, and
   returning the blood with target neutrophil cells with modified surface receptor expression therein from the extracorporeal device to the circulatory system of the patient via the outlet, wherein the IL-8 remains immobilized upon the at least one surface.

2. The method of claim 1 in which the blood is passed in a continuous loop from a blood vessel of the patient to contact the at least one surface and back to a blood vessel of the patient.

3. The method of claim 1 wherein the blood is passed continuously for at least a period of time from a blood vessel of the patient to contact the at least one surface and back to the blood vessel.

4. The method of claim 1 wherein the blood is passed discontinuously from a blood vessel of the patient to contact the at least one surface and back to the blood vessel.

5. The method of claim 1 wherein the target neutrophil cells are modified to treat sepsis.

6. The method of claim 1 wherein the extracorporeal device comprises a plurality of surfaces upon which IL-8 is immobilized.

7. The method of claim 6 wherein the plurality of surfaces comprises a plurality of hollow fibers.

8. The method of claim 6 wherein the plurality of surfaces comprises a plurality of beads.

9. The method of claim 1 wherein the IL-8 is immobilized via covalent bonding or ionic bonding to the at least one surface.

10. The method of claim 1 wherein the period of contact for target neutrophil cells is extended.

11. The method of claim 10 wherein the period of contact for target neutrophil cells is extended by the immobilization of an adhesion agent on the at least one surface, by at least one physiological characteristic of the at least one surface, or by a geometry of a volume through which the blood flows.

12. The method of claim 1 wherein cell surface receptors of the target neutrophil cells are downregulated.

13. A method of modifying the receptor expression of target neutrophil cells comprising:
    placing an inlet of an extracorporeal device in fluid connection with a circulatory system of a patient,
    placing an outlet of the extracorporeal device in fluid connection with the circulatory system of the patient,
    circulating fluid from the patient comprising blood or a fraction of the blood which includes the target neutrophil cells via the inlet and the outlet to pass fluid removed from the circulatory system of a patient, which includes the target neutrophil cells, through the extracorporeal device,
    inducing flow of the fluid through the extracorporeal device at a flow rate resulting in a cell residence time suitable for recirculation of the fluid to the patient, at least one surface within the extracorporeal device comprising IL-8 (interleukin 8) immobilized thereon via covalent or ionic bonding, the immobilized IL-8 effecting a predetermined modification of at least one cell surface receptor of the target neutrophil cells, and
    releasably interacting the IL-8 immobilized on at least one surface of the extracorporeal device with at least one cell surface receptor of the target neutrophil cells as the target neutrophil cells flow within the fluid thereover to modify the surface receptor expression of the target neutrophil cells, wherein the target neutrophil cells with modified surface receptor expression are released back into the flow of the fluid to be returned to the circulatory system of the patient via the outlet of the extracorporeal device.

\* \* \* \* \*